(12) United States Patent
Feder et al.

(10) Patent No.: US 7,329,650 B2
(45) Date of Patent: Feb. 12, 2008

(54) PEPTIDES AND PEPTIDE ANALOGUES DESIGNED FROM HFE PROTEIN AND THEIR USES IN THE TREATMENT OF IRON OVERLOAD DISEASES

(75) Inventors: John N. Feder, San Carlos, CA (US); Randall C. Schatzman, Daly City, CA (US); Pamela J. Bjorkman, Pasadena, CA (US); Melanie Bennett, Pasadena, CA (US); Jose Lebron, Pasadena, CA (US)

(73) Assignees: Bio-Rad Laboratories, Inc., Hercules, CA (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 11/184,459

(22) Filed: Jul. 18, 2005

(65) Prior Publication Data

US 2005/0282754 A1 Dec. 22, 2005

Related U.S. Application Data

(63) Continuation of application No. 09/901,956, filed on Jul. 9, 2001, now Pat. No. 6,924,265, which is a continuation of application No. 09/216,077, filed on Dec. 18, 1998, now Pat. No. 6,284,732.

(51) Int. Cl.
*A01N 43/04* (2006.01)

(52) U.S. Cl. ............... 514/44; 514/2; 514/13; 530/326; 536/23.1

(58) Field of Classification Search ...... None
See application file for complete search history.

(56) References Cited

U.S. PATENT DOCUMENTS

| | | | |
|---|---|---|---|
| 5,712,098 | A | 1/1998 | Tsuchihashi et al. |
| 6,284,732 | B1 | 9/2001 | Feder et al. |
| 6,924,265 | B2 | 8/2005 | Feder et al. |

FOREIGN PATENT DOCUMENTS

| | | |
|---|---|---|
| WO | WO 97/38137 | 10/1997 |
| WO | WO 98/56814 | 12/1998 |

OTHER PUBLICATIONS

"Computerized Drug Design: Still Promising, Not Yet Here", *Science*, vol. 256, pp. 441, Apr. 24, 1992.
Dadone et al. 1982, "Analysis of laboratory expression of the disease by genotype in 18 pedigrees", *AM. J. Clin. Pathol.*, 78:196-207.
Edwards et al. 1988, "Prevalence of Hemochromatosis Among 11,065 Presumably Healthy Blood Donors", *N. Engl. J. Med.*, 18:1355-1362.
Feder et al. 1998, "The hemochromatosis gene product complexes with the transferrin receptor and lowers its affinity for ligand binding", *Proc. Natl. Acad. Sci. U.S.A.*, 95:1472-1477.
Feder et al. 1996, "A novel MHC class I-like gene is mutated in patients with hereditary hemochromatosis", *Nature Genetics*, 13:399-408.
Feder et al. 1997, "The hemochromatosis founder mutation in HLA-H disrupts beta2-microglobulin interaction and cell surface expression", *J. Biol. Chem.*, 272:14025-14028.
Gross et al., 1998, "Co-trafficking of HFE, a nonclassical major histocompatibility complex class I protein, with the transferrin receptor implies a role in intracellular iron regulation", *J. Biol. Chem.*, 273:22068-22074.
Kosbor et al. 1983, "The production of monoclonal antibodies from human lymphocytes", *Immunology Today* 4:72.
Lebron et al. 1998, "Crystal structure of the hemochromatosis protein HFE and characterization of its interaction with transferrin receptor", *Cell* 93:111-123.
McLaren et al. 1995, "Prevalence of heterozygotes for hemochromatosis in the white population of the United States", *Blood* 86:2021-2027.
Ngo, et al 1994, 'Computational Complexity, Protein Structure Prediction, and the Levinthal Paradox,' The Protein Folding Problem and Tertiary Structurer Prediction. Ed. K. Merz and L. Le. Grand. Birkhauser, Boston MA. pp. 491-495.
Rudinger, J. 1976, Peptide Hormones (ed. J.A. Parsons). University Park Press. Baltimore. pp. 1-7.
Sampietro et al. 1998, "High prevalence of the His63 Asp HFE mutation in Italian patients with porphyria cutanea tarda", *Hepatology* 27:181-184.
Stagsted et al. 1993, "Amino acid residues essential for biological activity of a peptide derived from a major histocompatibility complex class I antigen", *Proc. Natl. Acad. Sci*, U.S.A. 90:7686-7690.
Stagsted et al. 1990, "Regulation of insulin receptor functions by a peptide derived from a major histocompatibility complex class I antigen", *Cell* 62:297-307.
Van Landeghem et al. 1998, "Interaction between haemochromatosis and transferrin receptor genes in multiple myeloma", *Lancet* 352:1285-1286.
Yaouanq et al. 1997, "Hemochromatosis Cys282Tyr mutation in pyridoxine-responsive sideroblastic anaemia", *Lancet* 349:1475-1476.

*Primary Examiner*—Anish Gupta
(74) *Attorney, Agent, or Firm*—Jones Day

(57) ABSTRACT

The present invention relates to peptides and peptide analogues designed from HFE protein. In particular, it relates to peptides and peptide analogues designed from an alpha-1 region of HFE protein which lowers the binding affinity of transferrin receptor for transferrin. Such compounds mimic HFE protein function, and reduce iron uptake and/or accumulation by a cell.

11 Claims, 1 Drawing Sheet

Figure 1:
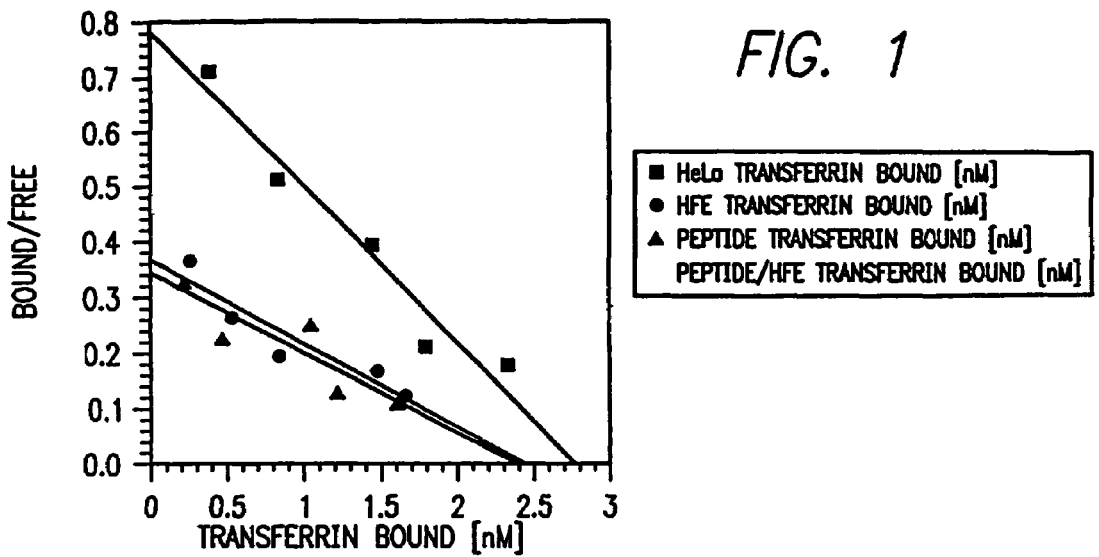

SEQUENCE LISTING

```
<160> NUMBER OF SEQ ID NOS: 8

<210> SEQ ID NO 1
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 1

Gly Trp Asp His Met Phe Thr Val Asp Phe Trp Thr Ile Met Glu Asn
 1               5                   10                  15

His

<210> SEQ ID NO 2
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 2

Gly Trp Ala His Met Phe Thr Val Asp Phe Trp Thr Ile Met Glu Asn
 1               5                   10                  15

His
```

```
<210> SEQ ID NO 3
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 3

Gly Trp Asp His Met Phe Thr Val Asp Phe Trp Thr Ile Met Glu Asn
  1               5                  10                  15

Ala

<210> SEQ ID NO 4
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 4

Gly Ala Asp His Met Phe Thr Val Asp Phe Trp Thr Ile Met Glu Asn
  1               5                  10                  15

His

<210> SEQ ID NO 5
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 5

Gly Trp Asp His Met Phe Thr Val Ala Phe Trp Thr Ile Met Glu Asn
  1               5                  10                  15

His

<210> SEQ ID NO 6
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 6

Gly Ala Asp His Met Phe Thr Val Ala Phe Trp Thr Ile Met Glu Asn
  1               5                  10                  15

His

<210> SEQ ID NO 7
<211> LENGTH: 51
<212> TYPE: DNA
<213> ORGANISM: Homo sapien

<400> SEQUENCE: 7
gggtgggatc acatgttcac tgttgacttc tggactatta tggaaaatca c      51

<210> SEQ ID NO 8
<211> LENGTH: 17
<212> TYPE: PRT
<213> ORGANISM: Artificial Sequence
<220> FEATURE:
<223> OTHER INFORMATION: Synthetic Peptide
```

```
<400> SEQUENCE: 8

Gly Trp Asp His Met Phe Thr Val Asp Phe Ala Thr Ile Met Glu Asn
1               5                   10                  15

His
```

PEPTIDES AND PEPTIDE ANALOGUES DESIGNED FROM HFE PROTEIN AND THEIR USES IN THE TREATMENT OF IRON OVERLOAD DISEASES

This application is a continuation of U.S. application Ser. No. 09/901,956, filed Jul. 9, 2001 now U.S. Pat. No. 6,924,265, which is a continuation of U.S. application Ser. No. 09/216,077, filed Dec. 18, 1998, now U.S. Pat. No. 6,284,732, the contents of which are herein incorporated by reference in their entirety for all purposes.

1. INTRODUCTION

The present invention relates to peptides and peptide analogues designed from HFE protein. In particular, it relates to peptides and peptide analogues designed from an alpha-1 region of HFE protein which lowers the binding affinity of transferrin receptor for transferrin. Such compounds mimic HFE protein function, and reduce iron uptake and/or accumulation by a cell.

2. BACKGROUND OF THE INVENTION

Hereditary hemochromatosis (HH) is a common genetic disorder characterized by excess iron deposition in the major organs of the body (Dadone et al., 1982, *AM. J. Clin. Pathol.* 78:196-207; Edwards et al., 1988, *N. Engl. J. Med.* 18:1355-1362; McLaren, et al., 1995, *Blood* 86:2021-2027; Bothwell et al., 1995, *The metabolic and molecular basis of inherited disease* (ed. C. R. Scriver, E. A.) 2237-2269, McGraw-Hill, New York; Bacon et al., 1996, *Hepatology, A textbook of liver disease* (eds. Zakim, D. & Boyer, T. D.) 1439-1472, W. B. Saunders, Philadelphia). A candidate gene linked to this disease, HFE, was identified by positional cloning (Feder et al., 1996, *Nature Genetics* 13:399-408). The gene, a novel member of the major histocompatibility complex (MHC) class I family, was found to have a mutation, cysteine 282→tyrosine (C282Y), in 83% of patient chromosomes (Feder et al., 1996, *Nature Genetics* 13:399-408). This mutation eliminates the ability of HFE to associate with $\beta_2$-microglobulin ($\beta_2$m) and prevents its expression on the cell surface (Feder, et al., 1997, *J. Biol. Chem.* 272:14025-14028).

Recently, the HFE protein was found to bind the transferrin receptor (TfR) at high affinity, and such binding, in turn, lowers TfR affinity for transferrin, the major iron-binding protein found in the serum (Feder et al., 1998, *Proc. Natl. Acad. Sci. U.S.A.* 95:1472-1477; Gross et al., 1998, *J. Biol. Chem.* 273:22068-22074. It has been shown that by lowering the TfR affinity for transferrin, the actual amount of iron taken up by the cell is decreased, as reflected by the disappearance of the cellular iron storage protein, ferritin. These observations suggest that HFE may be important in controlling iron homeostasis by interacting with the TfR.

A murine MHC class I molecule has been shown to interact with the insulin receptor on the cell surface. In addition, a 25 amino acid peptide derived from the alpha-1 domain (residues 61-85) of the murine MHC class I molecule H-2D$^k$ altered the function of the insulin receptor (Stagsted et al., 1990, *Cell* 62:297-307) by increasing rat adipocyte glucose uptake. This peptide was believed to act as a competitive inhibitor of intact MHC molecules on the cell surface. Additional studies have shown that by inhibiting insulin receptor internalization, the peptide activated a signal-transducing protein on the cell surface which led to increased glucose metabolism. A shortened version of the peptide containing 17 amino acids (residues 69-85) also exhibited similar activities (Stagsted et al., 1993, *Proc. Natl. Acad. Sci. U.S.A.* 90: 7686-7690). However, prior to the present invention, it was not known if a peptide derived from the HFE protein would mediate a biologic effect on the TfR.

3. SUMMARY OF THE INVENTION

The present invention relates to peptides and peptide analogues designed from HFE protein. In particular, it relates to peptides and peptide analogues designed from an alpha-1 region of HFE protein. More specifically, the invention relates to peptides and peptide analogues which lower the binding affinity of TfR for transferrin, methods of designing additional peptides and peptide analogues exhibiting similar activities, methods of using such compounds and pharmaceutical compositions thereof to inhibit iron uptake and/or accumulation by cells, as well as methods of using the compounds to treat iron overload diseases.

The invention is based, in part, on the Applicants' discovery that a peptide designed from an alpha-1 region of HFE protein inhibited cell-associated binding of transferrin. This peptide was generated on the basis of an amino acid sequence of HFE protein that made contact with TfR. The peptide lowers TfR binding affinity for transferrin, and enhances HFE inhibitory activities. The crystal structure of HFE protein shows that a tryptophan at position 81 (W81) of HFE could be at the TfR binding site (Lebron et al., 1998, *Cell* 93:111-123). This suggestion was confirmed by subsequent site directed mutagenesis, such that mutation of this residue to an alanine reduced the ability of HFE to bind TfR. Similarly, mutation of a peptide from Trp to Ala at residue 81 also reduced the ability of the peptide to inhibit cell-associated binding of transferrin. It is noted that the numbering of amino acid positions disclosed herein is based on the mature HFE protein. In contrast, the position of an amino acid mutation at residue 282 responsible for HH in the majority of patients is based on the precursor protein, which includes the leader peptide.

Generally, a compound of the present invention is a peptide or peptide analogue which can be 17 amino acids in length. In embodiments wherein the compound is a peptide, the peptide comprises an amino acid sequence that corresponds in primary sequence to an alpha-1 domain of HFE or a portion thereof. In certain embodiments, one or more amino acid residues within the peptide are substituted with other amino acid residues. Typically, such substitutions are conservative, i.e., the amino acid residues are replaced with other amino acid residues having similar physical and/or chemical properties. In embodiments wherein the compound is a peptide analogue, the analogue is obtained by replacing at least one amide linkage in the peptide with a substituted amide or an isostere of amide.

In an illustrative embodiment, a compound of the invention comprises the following formula:

$$Z_1\text{-}X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}Z_2 \quad (I)$$

wherein:
$X_1$ is an apolar residue;
$X_2$ is a hydrophobic residue;
$X_3$ is an acidic or an aliphatic residue;
$X_4$ is a basic residue;
$X_5$ is an apolar residue;
$X_6$ is an aromatic residue;
$X_7$ is a polar residue;
$X_8$ is an aliphatic residue;

$X_9$ is an acidic or an aliphatic residue;
$X_{10}$ is an aromatic residue;
$X_{11}$ is an aromatic residue;
$X_{12}$ is a polar residue;
$X_{13}$ is Ile;
$X_{14}$ is an apolar residue;
$X_{15}$ is an acidic residue;
$X_{16}$ is a polar residue;
$X_{17}$ is a basic or an aliphatic residue;
$Z_1$ is $H_2N$—, RHN— or, RRN—;
$Z_2$ is —C(O)R, —C(O)OR, —C(O)NHR, —C(O)NRR where each R is independently ($C_1$-$C_6$) alkyl, ($C_1$-$C_6$) alkenyl, ($C_1$-$C_6$) alkynyl, substituted ($C_1$-$C_6$) alky substituted ($C_1$-$C_6$) alkenyl or substituted ($C_1$-$C_6$) alkynyl; and
"-" is a covalent linkage.

In a preferred embodiment of the compounds of formula (I), $X_1$-$X_{17}$ is a peptide which corresponds in primary amino acid sequence to an alpha-1 domain of HFE protein, and which optionally may contain one or more conservative amino acid substitutions, or an analogue thereof. In a particularly preferred embodiment, the peptides and peptide analogues lower the binding affinity of TfR for transferrin. Therefore, such compounds are useful in inhibiting iron uptake and/or accumulation by cells. In yet another embodiment, the peptides and peptide analogues bind TfR and inhibit HFE binding to TfR, thereby increasing iron uptake by cells.

4. BRIEF DESCRIPTION OF THE DRAWINGS

FIG. 1. The G-(17)-H (Trp) wildtype peptide lowers cell-associated transferrin binding. HeLa cells alone (squares) bind transferrin at high affinity ($K_D$=approximately 3.3 nM). The presence of the G-(17)-H Trp wildtype peptide (triangles) acts in a manner equivalent to the 100 nM soluble HFE/$\beta_2$m heterodimers (circles) with respect to lowering the affinity of the TfR for transferrin ($K_D$=approximately 6.6-6.7 nM). G-(17)-H (Trp) wildtype peptide and 100 nM soluble HFE/$\beta_2$m heterodimers (diamonds) lower the affinity of the TfR to a greater extent than either of the two reagents alone ($K_D$=approximately 25 nM).

FIG. 2. The G-(17)-H (Ala) mutant peptide has little effect on cell-associated transferrin binding. HeLa cells alone (squares) bind transferrin at high affinity ($K_D$=approximately 4.8 nm in this experiment.) The presence of the G-(17)-H (Ala) mutant peptide (triangles) has an effect on the lowering the affinity of the TfR for transferrin ($K_D$=approximately 7.5 nM). 100 nM soluble HFE/$\beta_2$m heterodimers lower the affinity of the TfR for transferrin ($K_D$=approximately 14 nM in this experiment). G-(17)-H (Ala) mutant peptide and 100 nM soluble HFE/$\beta_2$m heterodimers (diamonds) do not act together to lower the affinity of the TfR for transferrin. The $K_D$ remains approximately 14 nM, the value obtained with 100 nM soluble HFE/$\beta_2$ heterodimers alone.

FIG. 3. The G-(17)-H (Ala) mutant peptide has little effect on cell-associated transferrin binding (Experiment #2). HeLa cells alone (squares) bind transferrin at high affinity ($K_D$=approximately 2.1 nM in this experiment.) The presence of the G-(17)-H (Ala) mutant peptide (diamonds) has a minor effect on lowering the affinity of the TfR for transferrin ($K_D$=approximately 2.8 nM). 100 nM soluble HFE/$\beta_2$m heterodimers (circles) lower the affinity of the TfR for transferrin ($K_D$=approximately 6.7 nM in this experiment). The G-(17)-H (Trp) peptide (triangles) also lower the affinity of the TfR for transferrin ($K_D$=approximately 4.1 nM in this experiment).

5. DETAILED DESCRIPTION OF THE INVENTION

The present invention relates to peptides and peptide analogues designed from HFE protein, which lower the binding affinity of TfR for transferrin. Although the specific procedures and methods described herein are exemplified using a specific peptide derived from an alpha-1 region of HFE, they are merely illustrative for the practice of the invention. Analogous procedures and techniques, as well as functionally equivalent peptides and peptide analogues, as will be apparent to those of skill in the art based on the detailed disclosure provided herein are also encompassed by the invention.

As used herein, the following terms shall have the following meanings:

"Alkyl:" refers to a saturated branched, straight chain or cyclic hydrocarbon radical. Typical alkyl groups include, but are not limited to, methyl, ethyl, propyl, isopropyl, butyl, isobutyl, t-butyl, pentyl, isopentyl, hexyl, and the like. In preferred embodiments, the alkyl groups are ($C_1$-$C_6$) alkyl, with ($C_1$-$C_3$) being particularly preferred.

"Substituted Alkyl:" refers to an alkyl radical wherein one or more hydrogen atoms are each independently replaced with other substituents.

"Alkenyl:" refers to an unsaturated branched, straight chain or cyclic hydrocarbon radical having at least one carbon-carbon double bond. The radical may be in either the cis or trans conformation about the double bond(s). Typical alkenyl groups include, but are not limited to, ethenyl, propenyl, isopropenyl, butenyl, isobutenyl, tert-butenyl, pentenyl, hexenyl and the like. In preferred embodiments, the alkenyl group is ($C_1$-$C_6$) alkenyl, with ($C_1$-$C_3$) being particularly preferred.

"Substituted Alkenyl:" refers to an alkenyl radical wherein one or more hydrogen atoms are each independently replaced with other substituents.

"Alkynyl:" refers to an unsaturated branched, straight chain or cyclic hydrocarbon radical having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is ($C_1$-$C_6$) alkynyl, with ($C_1$-$C_3$) being particularly preferred.

"Substituted Alkynyl:" refers to an alkynyl radical wherein one or more hydrogen atoms are each independently replaced with other substituents.

"Alkoxy:" refers to an —OR radical, where R is alkyl, alkenyl or alkynyl, as defined above.

"Aryl:" refers to an unsaturated cyclic hydrocarbon radical having a conjugated π electron system. Typical aryl groups include, but are not limited to, penta-2,4-diene, phenyl, naphthyl, anthracyl, azulenyl, indacenyl, and the like. In preferred embodiments, the aryl group is ($C_5$-$C_{20}$) aryl, with ($C_5$-$C_{10}$) being particularly preferred.

"Substituted Aryl:" refers to an aryl radical wherein one or more hydrogen atoms are each independently replaced with other substituents.

"Heteroaryl:" refers to an aryl group wherein one or more of the ring carbon atoms is replaced with another atom such as N, O or S. Typical heteroaryl groups include, but are not limited to, furanyl, thienyl, indolyl, pyrrolyl, pyranyl, pyridyl, pyrimidyl, pyrazyl, pyridazyl, purine, pyrimidine and the like.

"Substituted Heteroaryl:" refers to a heteroaryl radical wherein one or more hydrogen atoms are each independently replaced with other substituents.

5.1. Peptides and Peptide Analogues Designed from Alpha-1 Domain of HFE Protein Generally, a compound of the present invention is a peptide or peptide analogue. In embodiments wherein the compound is a peptide, the peptide corresponds in primary sequence to an alpha-1 domain of HFE protein or a portion thereof. In certain embodiments, one or more amino acid residues within the peptide are substituted with other amino acid residues. In embodiments wherein the compound is a peptide analogue, the analogue is obtained by replacing at least one amide linkage in the peptide with a substituted amide or isostere of amide.

A compound of the invention is illustrated by the following formula:

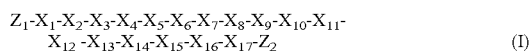

$$Z_1\text{-}X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}Z_2 \quad (I)$$

wherein:
- $X_1$ is an apolar residue;
- $X_2$ is a hydrophobic residue;
- $X_3$ is an acidic or an aliphatic residue;
- $X_4$ is a basic residue;
- $X_5$ is an apolar residue;
- $X_6$ is an aromatic residue;
- $X_7$ is a polar residue;
- $X_8$ is an aliphatic residue;
- $X_9$ is an acidic or an aliphatic residue;
- $X_{10}$ is an aromatic residue;
- $X_{11}$ is an aromatic residue;
- $X_{12}$ is a polar residue;
- $X_{13}$ is Ile;
- $X_{14}$ is an apolar residue;
- $X_{15}$ is an acidic residue;
- $X_{16}$ is a polar residue;
- $X_{17}$ is a basic or an aliphatic residue;
- $Z_1$ is $H_2N$—, RHN— or, RRN—;
- $Z_2$ is —C(O)R, —C(O)OR, —C(O)NHR, —C(O)NRR where each R is independently $(C_1\text{-}C_6)$ alkyl, $(C_1\text{-}C_6)$ alkenyl, $(C_1\text{-}C_6)$ alkynyl, substituted $(C_1\text{-}C_6)$ alky substituted $(C_1\text{-}C_6)$ alkenyl or substituted $(C_1\text{-}C_6)$ alkynyl; and
- "-" is a covalent linkage.

The designation $X_n$ in each case represents an amino acid at specified position in the compound. The amino acid residues may be the genetically encoded L-amino acids, naturally-occurring non-genetically encoded L-amino acids, synthetic L-amino acids, or D-enantiomers of all of the above. The amino acid notations used herein for the twenty genetically encoded L-amino acids and common non-encoded amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |

-continued

| Amino Acid | One-Letter Symbol | Common Abbreviation |
|---|---|---|
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-alanine | | bAla |
| 2,3-diaminopropionic acid | | Dpr |
| -α-aminoisobutyric acid | | Aib |
| N-methylglycine (sarcosine) | | MeGly |
| Ornithine | | Orn |
| Citrulline | | Cit |
| t-butylalanine | | t-BuA |
| t-butylglycine | | t-BuG |
| N-methylisoleucine | | MeIle |
| phenylglycine | | Phg |
| cyclohexylalanine | | Cha |
| Norleucine | | Nle |
| naphthylalanine | | Nal |
| Pyridylananine | | |
| 3-benzothienyl alanine | | |
| 4-chlorophenylalanine | | Phe(4-Cl) |
| 2-fluorophenylalanine | | Phe(2-F) |
| 3-fluorophenylalanine | | Phe(3-F) |
| 4-fluorophenylalanine | | Phe(4-F) |
| Penicillamine | | Pen |
| 1,2,3,4-tetrahydro-isoquinoline-3-carboxylic acid | | Tic |
| β-2-thienylalanine | | Thi |
| Methionine sulfoxide | | MSO |
| Homoarginine | | hArg |
| -acetyl lysine | | AcLys |
| 2,4-diamino butyric acid | | Dbu |
| p-aminophenylalanine | | Phe(pNH$_2$) |
| N-methylvaline | | MeVal |
| Homocysteine | | hCys |
| Homoserine | | hSer |
| ε-amino hexanoic acid | | Aha |
| δ-amino valeric acid | | Ava |
| 2,3-diaminobutyric acid | | Dab |

The compounds that are encompassed within the scope of the invention are partially defined in terms of amino acid residues of designated classes. The amino acids may be generally categorized into two main classes: hydrophilic amino acids and hydrophobic amino acids, depending primarily on the characteristics of the amino acid side chain. These main classes may be further divided into subcategories that more distinctly define the characteristics of the amino acid side chains. For example, hydrophilic amino acids include amino acids having acidic, basic or polar side chains; and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid exhibiting a hydrophobicity of greater than zero according to the normalized consensus hydrophobicity scale of Eisenberg et al. (1984, J. Mol. Biol. 179: 125-142). Examples of genetically encoded hydrophobic amino acids include Pro, Phe, Trp, Met, Ala, Gly, Tyr, Ile, Leu and Val. Examples of non-genetically encoded hydrophobic amino acids include t-BuA.

"Aromatic Amino Acid" refers to a hydrophobic amino acid having a side chain containing at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Examples of genetically encoded aromatic amino acids include Phe, Tyr and Trp. Commonly encountered non-genetically encoded aromatic amino acids include phenylglycine, 2-naphthylalanine, β-2-thienylalanine, 1,2,3,4-tetrahydroisoquinoline-3-carboxyli acid, 4-chloro-phenylalanine, 2-fluorophenylalanine, 3-fluorophenylalanine and 4-fluorophenylalanine.

"Apolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Examples of genetically encoded apolar amino acids include Gly, Leu, Val, Ile, Ala and Met. Examples of non-encoded apolar amino acids include Cha.

"Aliphatic Amino Acid" refers to a hydrophobic amino acid having an aliphatic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid exhibiting a hydrophilicity of less than zero according to the normalized consensus hydrophobicity scale of Eisenberg et al. (1984, J. Mol. Biol. 179: 125-142). Examples of genetically encoded hydrophilic amino acids include Thr, His, Glu, Asn, Gln, Asp, Arg, Ser and Lys. Examples of non-encoded hydrophilic amino acids include Cet and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include Asp and Glu.

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include Arg, Lys and His. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has one bond in which the pair of electrons shared in common by two atoms is held more closely by one of the atoms. Examples of genetically encoded polar amino acids include Ser, Thr, Asn and Gln. Examples of non-genetically encoded polar amino acids include citrulline, N-acetyl lysine and methionine sulfoxide.

The amino acid residue Cys is unusual in that it can form disulfide bridges with other Cys residues or other sulfanyl-containing amino acids. The ability of Cys residues (and other amino acids with —SH containing side chains) to exist in a peptide in either the reduced free —SH or oxidized disulfide-bridged form affects whether Cys residues contribute net hydrophilic or hydrophobic character to a peptide. While Cys exhibits hydrophobicity of 0.29 according to the normalized consensus scale of Eisenberg et al., it is understood that Cys is classified as a polar hydrophilic amino acid for the purpose of the present invention. Typically, cysteine-like amino acids generally have a side chain containing at least one thiol (SH) group. Examples of genetically encoded cysteine-like amino acids include Cys. Examples of non-genetically encoded cysteine-like amino acids include homocysteine and penicillamine.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded of which the peptides and peptide analogues of the invention may be composed include, but are not limited to, β-alanine (b-Ala) and other omega-amino acids such as 3-aminopropionic acid (Dap), 2,3-diamino-propionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diamninobutyric acid (Dab); 2,3-diaminobutyric acid (Dbu); p-aminophenylalanine (Phe (pNH$_2$)); N-methyl valine (MeVal); homocysteine (hCys) and homoserine (hSer). These amino acids also fall conveniently into the categories defined above.

The classifications of the above-described genetically encoded and non-encoded amino acids are summarized in Table 1, below. It is to be understood that Table 1 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, *CRC Practical Handbook of Biochemistry and Molecular Biology*, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded | Genetically Non-Encoded |
| --- | --- | --- |
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | L, V, I, A, M, G, P | T-BuA, T-BuG, MeIRe, Nle, MeVal, Cha, MeGly, Aib |
| Aliphatic | A, V, L, I | t-BuA, t-BuG, MeIle, Nle, MeVal, Cha, bAla, MeGly, Aib, Dpr, Aha |
| Hydrophilic | | |
| Acidic | D, E | |
| Basic | H, K, R | Dpr, Orn, hArg, Phe(p-NH$_2$), Dbu, Dab |
| Polar | C, Q, N, S, T | Cit, AcLys, MSO, hSer, bAla |
| Helix-Breaking | P, G | D-Pro and other D-amino acids (in L-peptides) |

In the compounds of formulae (I), the symbol "-" between amino acid residues generally designates a backbone interlinkage. Thus, the symbol "-" usually designates an amide linkage (—C(O)—NH). It is to be understood, however, that in all of the peptides described in the specific embodiments herein, one or more amide linkages may optionally be replaced with a linkage other than amide, preferably a substituted amide or an isostere of an amide linkage. Thus, while the various $X_n$ have generally been described in terms of amino acids, one having skill in the art will recognize that in embodiments having non-amide linkages, the term "amino acid" refers to other bifunctional moieties having side-chain groups similar to the side chains of the amino acids. For example, in embodiments having non-amide linkages, the phrase "acidic amino acid" refers to a bifunctional molecule capable of forming the desired backbone interlinkages and which has a side chain group similar to the side chain of an acidic amino acid. Substituted amides generally include groups of the formula —C(O)—NR, where R is ($C_1$-$C_6$) alkyl, ($C_1$-$C_6$) alkenyl, ($C_1$-$C_6$) alkynyl, substituted ($C_1$-$C_6$) alkyl, substituted ($C_1$-$C_6$) alkenyl or substituted ($C_1$-$C_6$) alkynyl. Isosteres of amide generally include, but are not limited to, —CH$_2$NH—, —CH$_2$S—, —CH$_2$CH$_2$, —CH═CH— (cis and trans), —C(O)CH$_2$—, —CH(OH)CH$_2$— and —CH$_2$SO—.

Compounds having such linkages and methods for preparing such compounds are well-known in the art (see, e.g., Spatola, 1983, *Vega Data* 1(3) for a general review); Spatola, 1983, "Peptide Backbone Modifications" In: *Chemistry and Biochemistry of Amino Acids Peptides and Proteins* (Weinstein, ed.), Marcel Dekker, New York, p.267 (general review); Morley, 1980, *Trends Pharm. Sci.* 1:463-468; Hudson et al., 1979, *Int. J. Prot. Res.* 14:177-185 (—CH$_2$NH—, —CH$_2$CH$_2$—); Spatola et al., 1986, *Life Sci.* 38:1243-1249 (—CH$_2$—S); Hann, 1982, *J. Chem. Soc. Perkin Trans. I.* 1:307-314 (—CH═CH—, cis and trans); Almquist et al., 1980, *J. Med. Chem.* 23:1392-1398 (—COCH$_2$—); Jennings-White et al., *Tetrahedron. Lett.* 23:2533 (—COCH$_2$—); European Patent Application EP 45665 (1982) CA:97:39405 (—CH(OH)CH$_2$—); Holladay et al., 1983, *Tetrahedron Lett.* 24:4401-4404 (—C(OH)CH$_2$—); and Hruby, 1982, *Life Sci.* 31:189-199 (—CH$_2$—S—).

Additionally, the compounds of the invention may have end modifications, denoted as $Z_1$ and $Z_2$ in formula (I). Such modifications can contain non-interfering amino acid residues. In one embodiments, the amino acid sequence LQLSQSLK (SEQ ID NO: 9) may be added to the amino terminus.

In a preferred embodiment of the invention, the compounds of formula (I) are defined as follows:

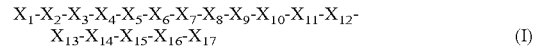

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17} \qquad (I)$$

wherein:
$X_1$ is an apolar amino acid;
$X_2$ is an aromatic amino acid;
$X_3$ is an acidic amino acid;
$X_4$ is a basic amino acid;
$X_5$ is an apolar amino acid;
$X_6$ is an aromatic amino acid;
$X_7$ is a polar amino acid;
$X_8$ is a aliphatic amino acid;
$X_9$ is a an acidic amino acid;
$X_{10}$ is an aromatic amino acid;
$X_{11}$ is an aromatic amino acid;
$X_{12}$ is a polar amino acid;
$X_{13}$ is Ile;
$X_{14}$ is an apolar amino acid;
$X_{15}$ is an acidic amino acid;
$X_{16}$ is a polar amino acid;
$X_{17}$ is a basic amino acid; and
"-" is an amide, substituted amide or an isostere of amide thereof.

In a particularly preferred embodiment, the compounds of the invention are those of formula (I) wherein:
$X_1$ is Gly;
$X_2$ is Trp or Ala;
$X_3$ is Asp or Ala;
$X_4$ is His;
$X_5$ is Met;
$X_6$ is Phe;
$X_7$ is Thr;
$X_8$ is Val;
$X_9$ is Asp or Ala;
$X_{10}$ is Phe;
$X_{11}$ is Trp;
$X_{12}$ is Thr;
$X_{13}$ is Ile;
$X_{14}$ is Met;
$X_{15}$ is Glu;
$X_{16}$ is Asn; and
$X_{17}$ is His or Ala.
$Z_1$ is H$_2$N;
$Z_2$ is —C(O)OH; and
"-" is an amide linkage.

In one preferred embodiment, "-" between each $X_n$ is —C(O)NH— or —C(O)NR—, where R is ($C_1$-$C_6$) alkyl, ($C_2$-$C_6$) alkenyl or ($C_2$-$C_6$) alkynyl, preferably ($C_1$-$C_6$) alkyl.

In another preferred embodiment, $X_4$ is His, $X_8$ is Val, $X_{11}$ is Trp and $X_{15}$ is Glu.

In still another preferred embodiment, $X_2$ is Trp, $X_3$ is Asp, $X_9$ is Asp and $X_{17}$ is His.

In yet another preferred embodiment, $X_2$ is Trp, $X_3$ is Ala, $X_9$ is Asp and $X_{17}$ is His.

In yet another preferred embodiment, $X_2$ is Trp, $X_3$ is Asp, $X_9$ is Asp and $X_{17}$ is Ala.

In still another preferred embodiment, the peptide comprises 17 residues.

Particularly preferred peptides of the invention include the following:

```
GWDHMFTVDFWTIMENH;        (SEQ ID NO:1)

GWAHMFTVDFWTIMENH;        (SEQ ID NO:2)

GWDHMFTVDFWTIMENA;        (SEQ ID NO:3)

GADHMFTVDFWTIMENH;        (SEQ ID NO:4)

GWDHMFTVAFWTIMENH.        (SEQ ID NO:5)

GADHMFTVAFWTIMENH.        (SEQ ID NO:6)
```

In all of the aforementioned embodiments of the invention, it is to be understood that the phrase "amino acid" also refers to bifunctional moieties having amino acid-like side chains, as previously described.

Generally, active peptides or peptide analogues of the invention are those that exhibit at least about 15% inhibition of TfR/transferrin interactions as measured in vitro assays such as those described in Section 6, infra. Preferably, active peptides of the invention or analogues thereof will exhibit at least about 20% to 50% or even 80% or more inhibition of TfR and transferrin binding interactions.

5.2. Preparation of Peptides and Peptide Analogues 5.2.1. Chemical Synthesis

The peptides of the invention or analogues thereof, may be prepared using virtually any art-known technique for the preparation of peptides and peptide analogues. For example, the peptides may be prepared in linear or non-cyclized form using conventional solution or solid phase peptide syntheses.

Formation of disulfide linkages, if desired, is generally conducted in the presence of mild oxidizing agents. Chemical oxidizing agents may be used, or the compounds may simply be exposed to atmospheric oxygen to effect these linkages. Various methods are known in the art, including those described, for example, by Tam, J. P. et al., 1979, *Synthesis* 955-957; Stewart et al., 1984, *Solid Phase Peptide Synthesis,* 2d Ed., Pierce Chemical Company Rockford, Ill.; Ahmed et al., 1975, *J. Biol. Chem.* 250:8477-8482; and Pennington et al., 1991 *Peptides* 1990 164-166, Giralt and Andreu, Eds., ESCOM Leiden, The Netherlands. An additional alternative is described by Kamber et al., 1980, *Helv Chim Acta* 63:899-915. A method conducted on solid supports is described by Albericio, 1985, *Int. J. Peptide Protein Res.* 26:92-97. Any of these methods may be used to form disulfide linkages in the peptides of the invention.

5.2.2. Recombinant Synthesis

If the peptide is composed entirely of gene-encoded amino acids, or a portion of it is so composed, the peptide or the relevant portion may also be synthesized using conventional recombinant genetic engineering techniques.

For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Maniatis et al., 1989, *Molecular Cloning A Laboratory Manual*, Cold Spring Harbor Laboratory, New York; and Ausubel et al., 1989, *Current Protocols in Molecular Biology*, Greene Publishing Associates and Wiley Interscience, New York). A preferred coding sequence contains the following nucleotide sequence:

```
GGG TGG GAT CAC ATG TTC ACT GTT GAC   (SEQ ID NO:7)

TTC TGG ACT ATT ATG GAA AAT CAC
```

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, *Nature* 310:511-514), or the coat protein promoter of TMV (Takamatsu et al., 1987, *EMBO J.* 6:307-311) may be used; alternatively, plant promoters such as the small subunit of RUBISCO (Coruzzi et al., 1984, *EMBO J.* 3:1671-1680; Broglie et al., 1984, *Science* 224:838-843) or heat shock promoters, e.g., soybean hsp17.5-E or hsp17.3-B (Gurley et al., 1986, *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, *Methods for Plant Molecular Biology, Academic Press,* NY, Section VIII, pp. 421-463; and Grierson & Corey, 1988, *Plant Molecular Biolog,* 2d Ed., Blackie, London, Ch. 7-9.

In one insect expression system that may be used to produce the peptides of the invention, *Autographa califor-*

*nica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, *J. Virol.* 46:584; Smith, U.S. Pat. No. 4,215,051). Further examples of this expression system may be found in *Current Protocols in Molecular Biology*, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, *Proc. Natl. Acad. Sci.* (*USA*) 81:3655-3659). Alternatively, the vaccinia 7.5 K promoter may be used, (see, e.g., Mackett et al., 1982, *Proc. Natl. Acad. Sci.* (*USA*) 79:7415-7419; Mackett et al., 1984, *J. Virol.* 49:857-864; Panicali et al., 1982, *Proc. Natl. Acad. Sci.* 79:4927-4931).

Other expression systems for producing the peptides of the invention will be apparent to those having skill in the art.

5.2.3. Purification Methods

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art.

For affinity chromatography purification, any antibody which specifically binds the peptides or peptide analogues may be used. For the production of antibodies, various host animals, including but not limited to rabbits, mice, rats, etc., may be immunized by injection with a linear peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, 1975, *Nature* 256:495-497, the human B-cell hybridoma technique, Kosbor et al., 1983, *Immunology Today* 4:72; Cote et al., 1983, *Proc. Natl. Acad. Sci. U.S.A.* 80:2026-2030 and the EBV-hybridoma technique (Cole et al., 1985, *Monoclonal Antibodies and Cancer Therapy*, Alan R. Liss, Inc., pp. 77-96 (1985)). In addition, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce peptide-specific single chain antibodies.

Antibody fragments which contain deletions of specific binding sites may be generated by known techniques. For example, such fragments include but are not limited to $F(ab')_2$ fragments, which can be produced by pepsin digestion of the antibody molecule and Fab fragments, which can be generated by reducing the disulfide bridges of the $F(ab')_2$ fragments. Alternatively, Fab expression libraries may be constructed (Huse et al., 1989, *Science* 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides of the invention. See, Scopes, 1984, *Protein Purification: Principles and Practice*, Springer-Verlag New York, Inc., NY, Livingstone, 1974, *Methods Enymology: Immunoaffinity Chromatogaphy of Proteins* 34:723-731.

5.3. Uses of Peptide and Peptide Analogues Designed from HFE Protein

The compounds of the present invention are useful for lowering TfR affinity for transferrin, thereby inhibiting iron accumulation in a cell. As a result, the compounds are particularly useful for the treatment of iron overload diseases. In a preferred embodiment of the invention, a compound of the invention enhances the biologic effects of HFE protein. Such compounds may be used for the treatment of conditions in which there is excess iron accumulation in a cell. Such conditions, include, but are not limited to, hemochromatosis and hemosiderosis.

While it is not intended to be bound by any theory, the compounds of the invention can decrease the total body iron burden in at least two ways. One, the presence of the peptides within cells of the intestinal mucosa, specifically the crypt cells of the small intestine, can act like endogenous HFE to control the amount of iron that is transported across the intestine and into the serum of an individual. This function will allow the peptides to act as a functional replacement of a mutated HFE protein in individuals with hemochromatosis, thereby correcting their condition and eliminating the need for individuals with hemochromatosis to undergo programs of the therapeutic phlebotomy. The peptides of the invention also have applications in the control of iron uptake for other diseases, where excess iron is a contributing factor in the etiology of the disease, such as porphyria cutanea tarda (Sampietro et al., 1997, *Hepatology* 27:181-184) and pyridoxine-responsive sideroblastic anemia (Yaouanq et al., 1997, *Lancet* 349:1475-1476).

The second way the peptides of the invention can lower the total body iron burden is by their presence in the sera of individuals. The peptides bind to the TfR, which is normally expressed on surface of cells, and decrease the total amount of iron that gradually accumulates within certain tissues as a result of elevated serum holo-transferrin, characteristic of hemochromatosis and other iron overload disorders that are secondary to the actual disease, such as thalassemias.

In addition, because rapidly dividing cells, such as tumor cells, have a particularly high requirement for iron, the compounds of the invention may be used to retard various types of tumor growth, by inhibiting the ability of the cells within the tumor of satisfying their iron requirements (Van Landeghem et al., 1998, *Lancet* 352:1285-1286). Hence, the compounds of the invention may be used for the treatment of cancer such as multiple myeloma.

5.3.1. Formulation and Route of Administration

The compounds of the invention may be administered to a subject per se or in the form of a pharmaceutical composition. Pharmaceutical compositions comprising the compounds of the invention may be manufactured by means of conventional mixing, dissolving, granulating, dragee making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration. For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

5.3.2. Effective Dosages

The compounds of the invention will generally be used in an amount effective to achieve the intended purpose. For use to treat or prevent iron overload diseases, the compounds of the invention, or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of TfR/transferrin-binding interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of iron overload diseases, treatment that may be used in combination with the compounds of the invention include, but are not limited to, phlebotomy.

5.3.3. Toxicity

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1996, In: *The Pharmacological Basis of Therapeutics*, 9$^{th}$ ed., Chapter 2, p. 29, Elliot M. Ross).

The invention having been described, the following examples are offered by way of illustration and not limitation.

6. EXAMPLE

A Peptide Corresponding to an Alpha-1 Region of HFE Protein Inhibits Cell-Associated Binding of Transferrin 6.1. Material and Methods 6.1.1. Peptide Synthesis The following two peptides were synthesized by Peninsula Laboratories (San Carlos, Calif.) to greater than 85% purity.

```
WILD-TYPE
G-(17)-H   +NH3-GWDHMFTVDFWTIMENH-COO-   (SEQ ID NO:1)
(Trp)

MUTANT
G-(17)-H   +NH3-GWDHMFTVDFATIMENH-COO-   (SEQ ID NO:8)
(Ala)
```

The peptides were solubilized in 0.1N HCl at a concentration of 1 mM for 30 min. at room temperature and stored at 4° C. An aliquot of this solution was diluted with DME plus mg/ml BSA to a concentration of 50 µM and neutralized with 1 M Hepes pH 7.5 to a final concentration of 25 mM Hepes.

6.1.2. Measurement of Cell-Associated Transferrin

HeLa cells were grown to 80-90% confluence at 37° C. at 5% $CO_2$. The cells were washed twice with PBS and detached from the plates using 4 mM EDTA/PBS. The cells were counted and diluted to $5\times10^6$ cells per ml in DMEM 1% fetal bovine serum (GIBCO) and $5\times10^5$ suspended cells were used for the TfR binding assay. Binding assays were all done in duplicate. Nonspecific binding was determined. The peptide/media solution was added to the cells in a final volume of 200 µl for 30 min. at 37 ° C. Labeled transferrin (New England Nuclear) was added to the cells at concentrations ranging from 0.5-15 nM. The reaction volume was 500 µL. Incubations were carried out for 20 min. for experiments performed at 37° C., or 90 min on ice for experiments performed at 4° C. At the end of the incubation, the cells were pelleted at 3,000 rpm for 2 min. The supernatant was decanted and radioactivity counted. The cells were gently washed four times by resuspending the cells with 1 ml ice-cold DMEM 1% fetal bovine serum and repelleting at low centrifugal force. During the washing steps the cells were kept at 4° C. After the final wash, the cells were resuspended in PBS and bound radioactivity was counted. The amount of transferrin bound to the cells was calculated by dividing the cpm bound to the cells by the cpm counted in the supernatant, this ratio was converted to a molar value by multiplying by the amount of transferrin used in the experiment. The $K_{cell\ association}$ and the apparent $K_D$ were calculated from the negative slope of the line generated by Scatchard analysis or by analyzing the binding curves utilizing nonlinear regression; both methods yielded essentially the same results.

To determine the amount of nonspecific transferrin binding, cells were simultaneously incubated under the same conditions but in the presence of 100× the molar concentration of cold holo-transferrin (Sigma). After 20 min (37° C.), the media was removed and counted in a Beckman 9600 scintillation counter. The cells were placed on ice and washed two times with media containing 1% fetal bovine serum, and then lysed with 1% SDS and counted. Specific cell-associated transferrin was calculated by subtracting the nonspecific cell-associated transferrin from the total. A second method was also used that utilized a constant amount of labeled transferrin (5 nM) and increasing amount of unlabeled transferrin to increase the total transferrin concentration. Identical results to those produced by the first method were obtained. Transferrin binding in HeLa cells at 4° C. was measured exactly as cell-associated transferrin except that the incubations were carried out at 4° C. instead of 37° C. and for 90 min instead of 20 min.

6.2. Results

HeLa cells bound transferrin with an apparent $K_D$ of approximately 3.5 nM (FIG. 1). In the presence of 100 nM soluble HFE/$\beta_2$m heterodimers, the $K_D$ was increased approximately 2-fold to 6.6 nM, indicating a decrease in the affinity of TfR for transferrin. In the presence of 50 µM G-(17)-H (Trp) peptide (SEQ ID NO:1), the $K_D$ was also increased approximately 2-fold to 6.6 nM. The combination of both 100 nM soluble HFE/$\beta_2$m heterodimers and 50 µM G-(17)-H (Trp) peptide, increased the $K_D$ to 24.8 nM. These data indicate that the G-(17)-H (Trp) peptide mimics the function of HFE protein and does not competitively inhibit the activities of HFE. Furthermore, the peptide enhances HFE protein function in inhibiting cell-associated binding of transferrin.

Figure 2:
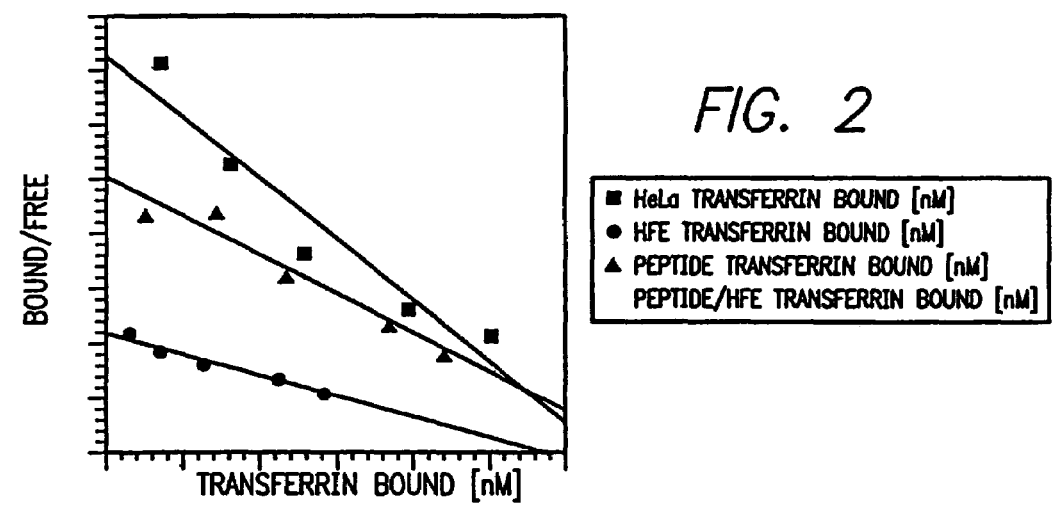

As a control for the specificity of the G-(17)-H (Trp) peptide, a mutant peptide, G-(17)-H (Ala) (SEQ ID NO:8), was also tested. The mutant peptide had an Ala substituted for the Trp at residue position 81 in the mature protein. Compared to addition of 100 nM of soluble HFE/$\beta_2$m heterodimers, which produced the characteristic increase in $K_D$, 50 µM G-(17)-H (Ala) had little effect on TfR affinity for transferrin (FIG. 2). In other words, the slope of the G-(17)-H (Ala) peptide line was closer to that obtained with HeLa cells alone than it was from that obtained with the addition of 100 nM soluble HFE/$\beta_2$m heterodimers. The minimum effect of the G-(17)-H (Ala) peptide on TfR affinity for transferrin was further demonstrated by the combination experiment, in which the peptide was mixed with 100 nM soluble HFE/$\beta_2$m heterodimers. While the wildtype peptide produced at least an additive effect with HFE/$\beta_2$m heterodimers, no additional increase in $K_D$ was observed by the addition of the mutant peptide to 100 nM soluble HFE/$\beta_2$m heterodimers. These results show that the alteration of a single amino acid residue, which is critical for the HFE/TfR interaction, can also affect the bioactivity of the 17 amino acid peptide.

Figure 3:
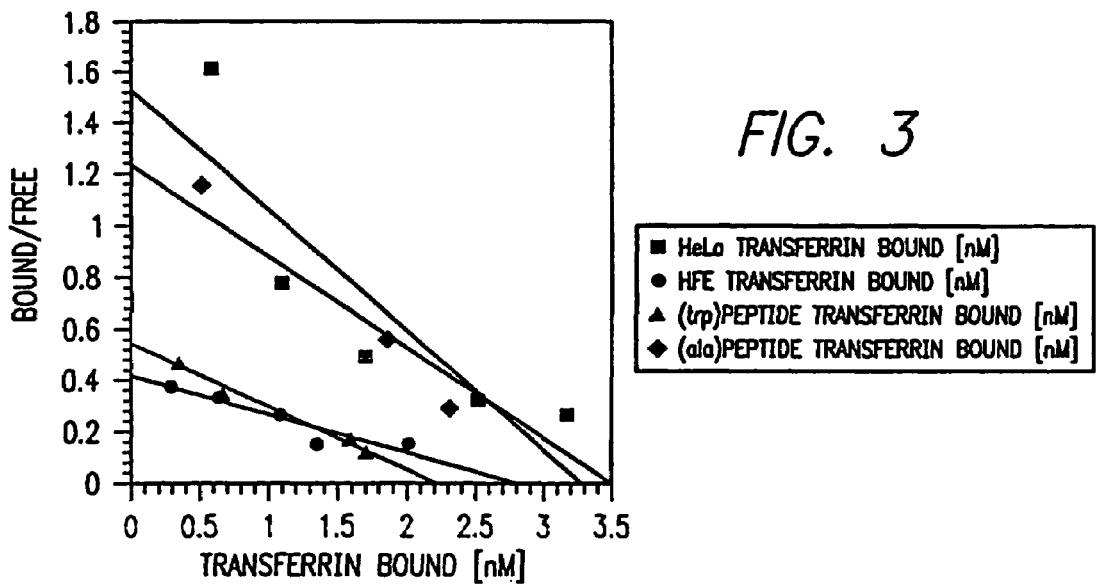

FIG. 3 shows the results of testing both the wildtype and mutant peptide side-by-side. In this experiment, HeLa cells exhibited a $K_D$ for transferrin of approximately 2.1 nM. The presence of 50 µM G-(17)-H (Ala) peptide had little effect on the TfR affinity for transferrin ($K_D$=2.8 nM). As observed in previous experiments, both the addition of 100 nM soluble HFE/$\beta_2$m heterodimers and 50 µM G-(17)-H (Trp) peptide produced a significant increase in $K_D$. These data confirmed that the mutant peptide G-(17)-H (Ala) is less effective than the wildtype peptide in altering transferrin receptor affinity for transferrin.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. An isolated nucleic acid encoding a peptide consisting of the formula:

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}$$

wherein:
$X_1$ is an apolar residue;
$X_2$ is a hydrophobic residue;
$X_3$ is an acidic or an aliphatic residue;
$X_4$ is a basic residue;
$X_5$ is an apolar residue;
$X_6$ is an aromatic residue;
$X_7$ is a polar residue;
$X_8$ is an aliphatic residue;
$X_9$ is an acidic or an aliphatic residue;
$X_{10}$ is an aromatic residue;
$X_{11}$ is an aromatic residue;
$X_{12}$ is a polar residue;
$X_{13}$ is Ile;
$X_{14}$ is an apolar residue;
$X_{15}$ is an acidic residue;
$X_{16}$ is a polar residue; and
$X_{17}$ is a basic or an aliphatic residue;
wherein the peptide reduces cell-associated binding of transferrin as measured in an in vitro cellular binding assay and produces at least an additive effect with soluble HFE/$\beta_2$m heterodimers in reducing cell-associated binding of transferrin as measured in the assay.

2. The nucleic acid of claim 1, wherein:
$X_1$ is an apolar amino acid;
$X_2$ is an aromatic amino acid;
$X_3$ is an acidic amino acid;
$X_4$ is a basic amino acid;
$X_5$ is an apolar amino acid;
$X_6$ is an aromatic amino acid;
$X_7$ is a polar amino acid;
$X_8$ is a aliphatic amino acid;
$X_9$ is a an acidic amino acid;
$X_{10}$ is an aromatic amino acid;
$X_{11}$ is an aromatic amino acid;
$X_{12}$ is a polar amino acid;
$X_{13}$ is Iie;
$X_{14}$ is an apolar amino acid;
$X_{15}$ is an acidic amino acid;
$X_{16}$ is a polar amino acid; and
$X_{17}$ is a basic amino acid.

3. The nucleic acid of claim 2, wherein:
$X_1$ is Gly;
$X_2$ is Trp or Ala;
$X_3$ is Asp or Ala;
$X_4$ is His;
$X_5$ is Met;
$X_6$ is Phe;
$X_7$ is Thr;
$X_8$ is Val;
$X_9$ is Asp or Ala;
$X_{10}$ is Phe;
$X_{11}$ is Trp;
$X_{12}$ is Thr;
$X_{13}$ is Ile;
$X_{14}$ is Met;
$X_{15}$ is Glu;
$X_{16}$ is Asn; and
$X_{17}$ is His or Ala.

4. The nucleic acid of claim 3, wherein the encoded polypeptide sequence is selected from the group consisting of SEQ ID NOs:1, 2, 3, 4, 5 and 6.

5. The nucleic acid of claim 4, wherein the encoded peptide sequence is SEQ ID NO:1.

6. The nucleic acid of claim 5, wherein the nucleic acid comprises the sequence of SEQ ID NO:7.

7. The nucleic acid of claim 3, wherein the encoded polypeptide sequence is selected from the group of SEQ ID NOs: 2, 3, 4, 5 and 6.

8. An expression vector comprising the nucleic acid according to claim 1.

9. The expression vector of claim 8, wherein the encoded peptide sequence comprises the amino acid sequence of SEQ ID NO: 1,2, 3,4, 5 or 6.

10. The expression vector of claim 8, wherein the polynucleotide sequence encodes a peptide comprising the sequence of SEQ ID NO:1.

11. The expression vector of claim 8, wherein the polynucleotide sequence comprises the sequence of SEQ ID NO:7.

* * * * *